United States Patent
Sonobe et al.

(10) Patent No.: US 6,830,753 B2
(45) Date of Patent: Dec. 14, 2004

(54) ADSORBENT FOR ORAL ADMINISTRATION

(75) Inventors: Naohiro Sonobe, Fukushima (JP); Michihito Ise, Tokyo (JP); Susumu Morimoto, Tokyo (JP); Hideyuki Yamato, Tokyo (JP); Satoshi Mitsuhashi, Saitama (JP); Haruhisa Hayashi, Tokyo (JP)

(73) Assignee: Kureha Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 10/267,795

(22) Filed: Oct. 10, 2002

(65) Prior Publication Data

US 2003/0118581 A1 Jun. 26, 2003

Related U.S. Application Data

(63) Continuation-in-part of application No. 10/119,720, filed on Apr. 11, 2002, now abandoned.

(30) Foreign Application Priority Data

Apr. 11, 2001 (JP) ........................................ 2001-112264

(51) Int. Cl.$^7$ ............................................... A61K 9/00
(52) U.S. Cl. ....................................... 424/400; 424/489
(58) Field of Search .................................. 424/400, 489

(56) References Cited

U.S. PATENT DOCUMENTS

| 4,681,764 A | * | 7/1987 | Endo et al. ................. 424/125 |
| 4,761,284 A | | 8/1988 | Nishimura |
| 5,573,761 A | | 11/1996 | Ise et al. |

FOREIGN PATENT DOCUMENTS

| EP | 0 595 715 A1 | 5/1994 |
| EP | 0 711 561 A2 | 5/1996 |
| EP | 1 249 241 A1 | 10/2002 |
| GB | 2 053 176 A | 2/1981 |

* cited by examiner

*Primary Examiner*—Michael G. Hartley
*Assistant Examiner*—Konata M. George
(74) *Attorney, Agent, or Firm*—Sugrue Mion, PLLC

(57) ABSTRACT

An adsorbent for an oral administration, comprising a porous spherical carbonaceous substance wherein a diameter is 0.01 to 1 mm, a specific surface area determined by a BET method is 700 m$^2$/g or more, a volume of pores having a pore diameter of 20 to 15000 nm is from not less than 0.04 mL/g to less than 0.10 mL/g, a total amount of acidic groups is 0.30 to 1.20 meq/g, and a total amount of basic groups is 0.20 to 1.00 meq/g, is disclosed.

11 Claims, 1 Drawing Sheet

ADSORBENT FOR ORAL ADMINISTRATION

CROSS REFERENCE TO RELATED APPLICATION

This is a continuation-in-part application of U.S. patent application Ser. No. 10/119,720 filed on Apr. 11, 2002 now abandoned.

BACKGROUND OF THE INVENTION

1. Field of the Invention

The present invention relates to an adsorbent for an oral administration, and a pharmaceutical composition comprising the adsorbent for an oral administration. The adsorbent for an oral administration, according to the present invention, comprises a porous spherical carbonaceous substance having a pore volume within a specific scope, and exhibits an excellent adsorbability of harmful toxins in gastrointestinal tracts, despite a low adsorbability of useful components such as digestive enzymes in a body, when orally administered. Further, when the present adsorbent is administered to patients suffering from liver or renal diseases, a remarkable curative effect can be obtained.

2. Description of the Related Art

In patients with a lack of a renal function or a liver function, harmful toxic substances are accumulated or formed in bodies, such as blood, with a progress of a disorder of the organ functions, and thus, an encephalopathia occurs such as a disturbance of consciousness or uremia. There is a growing number of such patients from year to year, and therefore, a development of an organ-substitute apparatus or medicament having a function to remove toxic substances from bodies, in place of such defective organs, has become a serious problem. A method for removing toxic substances by a hemodialysis is prevalent as an artificial kidney at present. Nevertheless, the hemodialysis-based artificial kidney requires a special apparatus, and thus, a skilled specialist is required from a safely operating standpoint of view. Further, blood must be taken from a patient's body, and thus, there are disadvantages in that patients must bear high physical, mental and economic burdens. Accordingly, hemodialysis is not satisfactory.

Recently, as a means of remedying the above disadvantages, an oral adsorbent which can be orally administered and cure a disorder of renal and liver functions has received considerable attention. Specifically, an adsorbent disclosed in Japanese Examined Patent Publication (Kokoku) No. 62-11611 [=U.S. Pat. No. 4,681,764] comprises a porous spherical carbonaceous substance having particular functional groups; has a high safety factor and is stable to a body; and has a useful selective adsorbability, that is, an excellent adsorbability of harmful substances in the presence of a bile acid in an intestine, and a low adsorbability of useful substances such as digestive enzymes in the intestine. For these reasons, the oral adsorbent is widely and clinically used for a patient suffering from a disorder of a liver or renal function, as an adsorbent having few side effects such as constipation.

SUMMARY OF THE INVENTION

The inventors of the present invention engaged in intensive research to develop an oral adsorbent having a more excellent selective adsorbability than the above-mentioned oral adsorbent comprising the porous spherical carbonaceous substance, and surprisingly found that a porous spherical carbonaceous substance having a pore volume within a special scope exhibits an excellent selective adsorbability, that is, an excellent adsorbability of β-aminoisobutyric acid, which is a toxic substance in a renal disease, despite a low adsorbability of useful substances, for example, digestive enzymes, such as α-amylase, less than that of the adsorbent disclosed in Japanese Examined Patent Publication (Kokoku) No. 62-11611. Further, the present inventors also found that the newly found porous spherical carbonaceous substance has few side effects such as constipation, and exhibits an excellent function as an oral medicament for treating a liver or renal disease.

The present invention is based on the above findings.

Accordingly, the object of the present invention is to provide an oral adsorbent exhibiting an excellent selective adsorbability.

Other objects and advantages of the present invention will be apparent from the following description.

In accordance with the present invention, there is provided an adsorbent for an oral administration, comprising a porous spherical carbonaceous substance wherein a diameter is 0.01 to 1 mm, a specific surface area determined by a BET method is 700 $m^2/g$ or more, a volume of pores having a pore diameter of 20 to 15000 nm is from not less than 0.04 mL/g to less than 0.10 mL/g, a total amount of acidic groups is 0.30 to 1.20 meq/g, and a total amount of basic groups is 0.20 to 1.00 meq/g.

DESCRIPTION OF THE PREFERRED EMBODIMENTS

Figure 1:
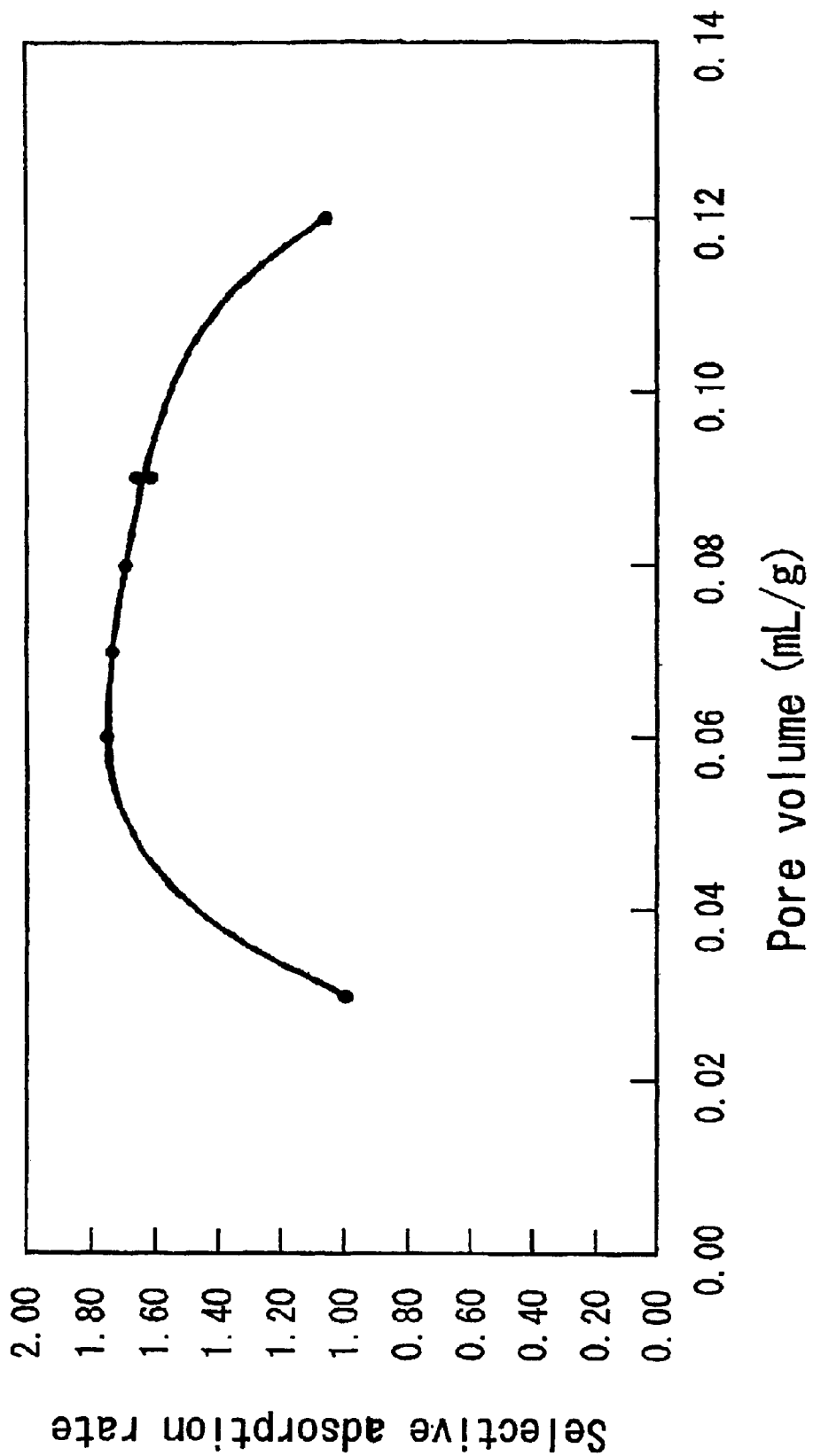
FIG. 1 is a graph showing the relationship between a selective adsorption rate and a pore volume of a carbonaceous adsorbent for the seven (7) carbonaceous adsorbents prepared in Examples 1 to 5 and Comparative Examples 1 to 2.

The porous spherical carbonaceous substance used as the adsorbent for an oral administration according to the present invention has a pore volume within a specific scope. That is, a volume of pores having a diameter of 20 to 15000 nm ranges from not less than 0.04 mL/g to less than 0.10 mL/g. On the other hand, the above-mentioned Japanese Examined Patent Publication (Kokoku) No. 62-11611 discloses an adsorbent comprising a porous spherical carbonaceous substance wherein a volume of voids having a pore radius of 100 to 75000 angstrom, that is, a volume of pores having a diameter of 20 to 15000 nm, is 0.1 to 1 mL/g. Further, the Japanese Publication mentions that the adsorbent exhibits excellent adsorbability of octopamine and α-aminobutyric acid, which is a substance causing a hepatic encephalopathy, dimethylamine, β-aminoisobutyric acid, or aspartic acid, which is a toxic substance or a precursor thereof in a renal disease, or a water-soluble basic or amphoteric substance, such as arginine, in the presence of a bile acid, despite a low adsorbability of useful substances, for example, digestive enzymes. In Examples 1 to 3 of the above-mentioned Japanese Examined Patent Publication (Kokoku) No. 62-11611, adsorbents wherein a volume of voids having a pore radius of 37.5 to 75000 angstrom is 0.20 to 0.23 mL/g were actually prepared, and an excellent adsorbability of β-aminoisobutyric acid, γ-amino-n-butyric acid, dimethylamine, and octopamine was actually confirmed.

On the contrary, the inventors of the present invention found that, as shown in the working Examples of the present specification, when the volume of pores having a pore diameter of 20 to 15000 nm is adjusted to range from not less than 0.04 mL/g to less than 0.10 mL/g, an adsorbability of α-amylase that is a useful substance, is significantly lowered, while maintaining a high adsorbability of β-aminoisobutyric acid, that is a toxic substance. When the volume of pores having a pore diameter of 20 to 15000 nm is increased, the useful substances such as digestive enzymes are more easily adsorbed. Therefore, a smaller volume of pores having a pore diameter of 20 to 15000 nm is preferable from a viewpoint that an adsorption of useful substances is reduced. On the other hand, if the volume of pores having such a pore diameter becomes too small, the adsorption of harmful substances is lowered.

Therefore, in the adsorbent for an oral administration, a ratio (T/U) of an adsorption amount (T) of toxic substances to an adsorption amount (U) of useful substances, that is, a selective adsorption rate, is important. For example, the selective adsorption rate of the porous spherical carbonaceous substance can be evaluated by the ratio (Tb/Ua) of an adsorption amount (Tb) of DL-β-aminoisobutyric acid (toxic substance) to an adsorption amount (Ua) of α-amylase (useful substance). More particularly, the selective adsorption rate can be evaluated by, for example, an equation:

$$A=Tb/Ua$$

wherein A denotes a selective adsorption rate, Tb denotes an adsorption amount of DL-β-aminoisobutyric acid, and Ua denotes an adsorption amount of α-amylase.

The porous spherical carbonaceous adsorbent of the present invention exhibits an excellent selective adsorption rate when the volume of pores having a pore diameter of 20 to 15000 nm ranges from not less than 0.04 mL/g to less than 0.10 mL/g, and a more excellent selective adsorption rate when the volume of pores having a pore diameter of 20 to 15000 nm ranges from not less than 0.05 mL/g to less than 0.10 mL/g.

The porous spherical carbonaceous substance used as the adsorbent for an oral administration according to the present invention has a diameter of 0.01 to 1 mm. When the diameter of the porous spherical carbonaceous substance becomes less than 0.01 mm, an exterior surface area of the porous spherical carbonaceous substance is increased, and useful substances such as digestive enzymes are easily adsorbed. When the diameter is more than 1 mm, a diffusion distance of toxic substances into the inside of the porous spherical carbonaceous substance is increased, and an adsorption rate is lowered. The diameter is preferably 0.02 to 0.8 mm. The expression that "a diameter is Dl to Du" as used herein means that a screen passing percentage (%) in a range of a screen opening Dl to Du is 90% or more in a particle-sizes accumulating standard curve prepared in accordance with JIS K 1474 as mentioned below in relation with a method for determining an average particle diameter.

The porous spherical carbonaceous substance used as the adsorbent for an oral administration according to the present invention has a specific surface area (referred to as "SSA" hereinafter) determined by a BET method of 700 m$^2$/g or more. When the porous spherical carbonaceous substance has the SSA of less than 700 m$^2$/g, an adsorbability of toxic substances is lowered. The SSA is preferably 800 m$^2$/g or more. The upper limit of the SSA is not particularly limited, but the SSA is preferably 2500 m$^2$/g or less in view of a bulk density and strength.

The porous spherical carbonaceous substance used as the adsorbent for an oral administration according to the present invention has a special constitution of functional groups, that is, a total amount of acidic groups is 0.30 to 1.20 meq/g, and a total amount of basic groups is 0.20 to 1.00 meq/g. When the porous spherical carbonaceous substance does not satisfy the functional-groups requirement, that the total amount of acidic groups is 0.30 to 1.20 meq/g, and the total amount of basic groups is 0.20 to 1.00 meq/g, the adsorbability of the harmful substances is lowered. In the functional-groups requirement, the total amount of acidic groups is preferably 0.30 to 1.00 meq/g and the total amount of basic groups is preferably 0.30 to 0.60 meq/g. When the adsorbent for an oral administration according to the present invention is used as a medicament for treating a liver or renal disease, a preferable functional-groups constitution is that the total amount of acidic groups is 0.30 to 1.20 meq/g, the total amount of basic groups is 0.20 to 1.00 meq/g, a phenolic hydroxyl group is 0.20 to 0.70 meq/g, and a carboxyl group is 0.15 meq/g or less, and a ratio (a/b) of the total amount of acidic groups (a) to the total amount of basic groups (b) is 0.40 to 2.5, and a relation [(b+c)−d] between the total amount of basic groups (b), the phenolic hydroxyl group (c), and the carboxyl group (d) is 0.60 or more.

The porous spherical carbonaceous substance used as the adsorbent for an oral administration according to the present invention may be prepared by, for example, the following methods.

First, a dicyclic or tricyclic aromatic compound or a mixture thereof having a boiling point of 200° C. or more is added as an additive to a pitch such as a petroleum pitch or a coal pitch. The whole is heated and mixed, and then shaped to obtain a shaped pitch. The porous spherical carbonaceous substance is for an oral administration, and the raw material must have a sufficient purity from a safety standpoint, and have stable properties.

Thereafter, the shaped pitch is dispersed and granulated in hot water at 70 to 180° C., with stirring, to obtain a microspherical shaped pitch. Further, the additive is extracted and removed from the shaped pitch by a solvent having a low solubility to the pitch but a high solubility to the additive. The resulting porous pitch is oxidized by an oxidizing agent to obtain a porous pitch having an infusibility to a heat. The resulting infusible porous pitch is treated at 800 to 1000° C. in a gas flow such as steam or carbon dioxide gas reactive with carbon to obtain a porous carbonaceous substance.

Then, the resulting porous carbonaceous substance is oxidized in a temperature range of 300 to 800° C., preferably 320 to 600° C. in an atmosphere containing 0.1 to 50% by volume, preferably 1 to 30% by volume, particularly preferably 3 to 20% by volume of oxygen, and thereafter reduced in a temperature range of 800 to 1200° C., preferably 800 to 1000° C., in an atmosphere of a non-oxidizable gas to obtain the porous spherical carbonaceous substance used as the adsorbent for an oral administration according to the present invention.

In the above method, the atmosphere containing oxygen in the particular amount may be pure oxygen, or nitrogen oxides or air as the oxygen source. As the atmosphere inert against carbon, for example, nitrogen, argon or helium may be used alone or in the form of a mixture thereof.

The purposes of the addition of the aromatic compound to the raw pitch are that a flowability of the raw pitch is enhanced by lowering a softening point of the raw pitch whereby the granulation thereof is made easier, and the porous pitch is produced by extracting and removing the additive from the shaped pitch, whereby a structure control and a calcination of the carbonaceous material by oxidization in the subsequent steps is made easier. As the additive, for example, naphthalene, methylnaphthalene, phenylnaphthalene, benzyl-naphthalene, methylanthracene, phenanthrene, or biphenyl may be used alone or in a mixture thereof. An amount of the additive added to the pitch is preferably 10 to 50 parts by weight of the aromatic compound with respect to 100 parts by weight of the pitch.

It is preferable that the pitch and the additive are mixed under a melted condition with heating, to achieve a homogeneous mixing. Further, it is preferable that the mixture of the pitch and the additive is shaped to form particles having a particle size of about 0.01 to 1 mm, to control the particle size (diameter) of the resulting porous spherical carbonaceous adsorbent. The shaping may be conducted during the melted condition, or by grinding the mixture after it has cooled.

A preferable solvent used to extract and remove the additive from the mixture of the pitch and the additive may be, for example, an aliphatic hydrocarbon, such as butane, pentane, hexane, or heptane, a mixture comprising an aliphatic hydrocarbon as a main component, such as naphtha or kerosene, or an aliphatic alcohol, such as methanol, ethanol, propanol, or butanol.

The additive may be removed from the shaped mixture by extracting the additive with the solvent from the shaped mixture of the pitch and the additive, while maintaining the shape. It is assumed that, upon the extraction, through-holes of the additive are formed in the shaped product, and a shaped pitch having a uniform porosity can be obtained. In this connection, the size of through-holes of the additive (i.e., pore volume) may be controlled by a conventional method, for example, by controlling an amount of the additive, or a precipitating temperature (cooling temperature) of the additive in the granulating step of the shaped pitch. Further, when the resulting shaped pitch is crosslinked by oxidation, the pore volume generated by extracting the additive is affected by a condition of the treatment. For example, if it is strongly crosslinked by oxidation, a heat contraction caused by a heat treatment is small, and thus the pores obtained by extracting the additive tend to be maintained.

Then, the resulting porous shaped pitch is crosslinked by oxidation, that is, the resulting porous shaped pitch is oxidized by an oxidizing agent, preferably at room temperature to 300° C. to obtain the porous infusible shaped pitch having a non-fusibility to heat. As the oxidizing agent, for example, oxygen gas ($O_2$), or a gas mixture prepared by diluting oxygen gas ($O_2$) with air or nitrogen may be used.

Properties of the porous spherical carbonaceous substance used as the adsorbent for an oral administration according to the present invention, namely, the average particle diameter, the specific surface area, the pore volume, the total amount of acidic groups, and the total amount of basic groups are measured by the following methods.

(1) An Average Particle Diameter

A particle-sizes accumulating standard curve is prepared in accordance with JIS K 1474 for the porous spherical carbonaceous substance. The average particle diameter is determined from a screen opening (mm) at an intersection point with a line that is horizontal to an abscissa axis and starts from an intersection point in the particle-sizes accumulating standard curve with a perpendicular line from a 50% point of the abscissa axis.

(2) A Specific Surface Area

An amount of gas adsorbed is measured by a specific surface area measuring apparatus (for example, Flow Sorb II 2300 manufactured by MICROMERITICS) in accordance with a gas adsorbing method of a continuous flow for the porous spherical carbonaceous substance sample, and a specific surface area can be calculated by a BET equation. More particularly, the porous spherical carbonaceous substance is charged as a sample in a sample tube. A helium gas stream containing 30% by volume of nitrogen is passed through the sample tube, and an amount of nitrogen adsorbed to the porous spherical carbonaceous substance sample is measured by the following procedures. Specifically, the sample tube is cooled to −196° C., whereby nitrogen is adsorbed to the porous spherical carbonaceous substance sample, and then the temperature of the sample tube is raised to room temperature. During the raising the temperature, nitrogen is emitted from the porous spherical carbonaceous substance sample. The amount of the emitted nitrogen is measured by a heat conductivity type detector as an amount (v) of gas adsorbed.

A value $v_m$ is calculated in accordance with a one-point method (relative pressure x=0.3) by a nitrogen adsorption at a temperature of liquid nitrogen, using an approximate equation:

$$v_m = 1/(v \cdot (1-x))$$

derived from the BET equation. Then, a specific surface area of the sample is calculated by an equation:

$$\text{specific surface area} = 4.35 \times v_m (m^2/g).$$

In the above equations, $v_m$ is an adsorption amount ($cm^3/g$) necessary to form a monomolecular layer on a surface of the sample, v is an adsorption amount ($cm^3/g$) actually found, and x is a relative pressure.

(3) A Pore Volume by a Mercury Injection Method

The pore volume can be measured by a mercury porosimeter (for example, AUTOPORE 9200 manufactured by MICROMERITICS). The porous spherical carbonaceous substance is charged as a sample in a sample vessel, and degassed under a pressure of 2.67 Pa or less for 30 minutes. Then, mercury is introduced into the sample vessel, a pressure applied is gradually increased (maximum pressure= 414 MPa) to force the mercury into the micropores in the porous spherical carbonaceous substance sample. A pore volume distribution of the porous spherical carbonaceous substance sample is measured from a relationship between the pressure and an amount of forced mercury by equations as mentioned below. Specifically, a volume of mercury inserted into the porous spherical carbonaceous substance sample while a pressure is applied is increased from a pressure (0.07 MPa) corresponding to a pore diameter of 15 μm to the maximum pressure (414 Mpa) corresponding to a pore diameter of 3 nm. A pore diameter can be calculated as follows. When mercury is forced into a cylindrical micropore having a diameter (D) by applying a pressure (P), a surface tension (γ) of mercury is balanced with a pressure acting on a section of the micropore, and thus, a following equation is held:

$$-\pi D \gamma \cos \theta = \pi (D/2)^2 \cdot P$$

wherein θ is a contact angle of mercury and a wall of the micropore. Therefore, a following equation:

$$D = (-4\gamma \cos \theta)/P$$

is held.

In the present specification, the relationship between the pressure (P) and the pore diameter (D) is calculated by an equation:

$$D = 1.27/P$$

given that a surface tension of mercury is 484 dyne/cm, a contact angle of mercury and carbon is 130°, a unit of the pressure P is Mpa, and a unit of the pore diameter D is μm. The volume of pores having a pore diameter of 20 to 15000 nm in the present invention corresponds to a volume of mercury inserted by applying a pressure increasing from 0.07 Mpa to 63.5 Mpa.

(4) Total Amount of Acidic Groups

The total amount of acidic groups is an amount of NaOH consumed, which may be determined by adding 1 g of the porous spherical carbonaceous substance sample, after being crushed to form particles having a size of less than 200 mesh, to 50 mL of a 0.05N NaOH solution; shaking the mixture for 48 hours; then filtering out the porous spherical carbonaceous substance sample; and titrating until neutralization.

(5) Total Amount of Basic Groups

The total amount of basic groups is an amount of HCl consumed, which may be determined by adding 1 g of the porous spherical carbonaceous substance sample after being crushed to form particles having a less than 200 mesh size, to 50 mL of a 0.05N HCl solution; shaking the mixture for 24 hours; then filtering out the porous spherical carbonaceous substance sample; and titrating until neutralization.

The porous spherical carbonaceous substance used as the adsorbent for an oral administration according to the present invention contains both ionic groups, that is, acidic groups and basic groups, as above, and exhibits an excellent selective adsorbability of toxic substances under an intestinal condition. Therefore, the porous spherical carbonaceous substance may be used as an adsorbent for an oral administration for treating or preventing a renal disease or a liver disease.

As the renal disease, there may be mentioned, for example, chronic renal failure, acute renal failure, chronic pyelonephritis, acute pyelonephritis, chronic nephritis, acute nephritic syndrome, acute progressive nephritic syndrome, chronic nephritic syndrome, nephrotic syndrome, nephrosclerosis, interstitial nephritis, tubulopathy, lipoid nephrosis, diabetic nephropathy, renovascular hypertension, or hypertension syndrome, or secondary renal diseases caused by these primary diseases, or a light renal failure before a dialysis therapy, and may be used in an improvement of a light renal failure before a dialysis therapy or a disease condition for a patient during a dialysis therapy (see "Clinical Nephrology", Asakura-shoten, Nishio Honda, Kenkichi Koiso, and Kiyoshi Kurokawa, 1990; and "Nephrology" Igaku-shoin, Teruo Omae and Sei Fujimi, ed., 1981).

As the liver disease, there may be mentioned, for example, fulminant hepatitis, chronic hepatitis, viral hepatitis, alcoholic hepatitis, hepatic fibrosis, liver cirrhosis, hepatic cancer, autoimmune hepatitis, drug allergic hepatopathy, primary biliary cirrhosis, tremor, encephalopathia, dysbolism, or dysfunction. Further, the porous spherical carbonaceous substance can be used in a treatment of a disease caused by toxic substances in a body, such as psychosis.

When the adsorbent for an oral administration according to the present invention is used as a medicament for a treatment of a liver or renal disease, a dosage thereof depends on the subject (human or other animal), age, individual differences, disease conditions, and so on. Therefore, in some cases, a dosage outside of the following dosage may be appropriate, but in general, the oral dosage in the case of a human is usually 1 to 20 g of the adsorbent per day, wherein the daily dosage may be divided into three to four portions. The dosage may appropriately vary with the disease conditions. The formulation may be administered in any form, such as powders, granules, tablets, sugar-coated tablets, capsules, suspensions, sticks, divided packages, or emulsions. In the case of capsules, the usual gelatin capsules, or if necessary, enteric capsules may be used. In the case of tablets, the formulations must be broken into the original fine particles inside the body. The adsorbent may be used as a mixture with an electrolyte-controlling agent, such as an aluminum gel or KAYEXALATE® (Windrop Lab, U.S.A.) or other agents.

EXAMPLES

The present invention will now be further illustrated by, but is by no means limited to, the following Examples.

In the following Examples, an adsorption test of α-amylase and an adsorption test of DL-β-aminoisobutyric acid were carried out in accordance with the following methods, and the selective adsorption rate was calculated by the following method.

(1) Adsorption Test of α-Amylase

The porous spherical carbonaceous substance sample was dried, and 0.125 g of the dried sample was accurately weighed and charged into a conical flask equipped with a ground-in stopper. On the other hand, 0.100 g of α-amylase (liquefied type) was accurately weighed and dissolved by adding a phosphate buffer (pH 7.4) to prepare a stock solution having an accurate volume of 1000 mL. The stock solution in an accurate amount of 50 mL was charged to the conical flask equipped with a ground-in stopper. The flask was shaken at 37±1° C. for 3 hours. The product in the flask was filtered with suction through a 0.65 μm membrane filter. A first filtrate (about 20 mL) was discarded, and a subsequent filtrate (about 10 mL) was taken as a sample solution.

Further, the same procedures were repeated except that only a phosphate buffer (pH 7.4) was used, to obtain a filtrate as an amendment solution. The sample solution and the amendment solution were analyzed by an absorptiometric analysis, using a phosphate buffer (pH 7.4) as a control. The absorbance at a wavelength of 282 nm was measured. A difference between the absorbance of the sample solution and the absorbance of the amendment solution was taken as a test absorbance.

A standard curve was prepared by adding the α-amylase stock solution in an accurate amount of 0 mL, 25 mL, 50 mL, 75 mL, or 100 mL to a measuring flask, adding a phosphate buffer (pH 7.4) to 100 mL, and measuring an absorbance at a wave length of 282 nm. From the test absorbance and the standard curve, an amount (mg/dL) of remaining α-amylase in the solution was calculated.

To measure a dependence on an amount of the porous spherical carbonaceous substance sample, the same procedures were repeated except that an amount of the porous spherical carbonaceous substance sample used was 0.500 g, and the test absorbance was measured and the amount of remaining α-amylase in the solution was calculated as above.

(2) Adsorption Test of DL-β-aminoisobutyric Acid

The porous spherical carbonaceous substance sample was dried, and 2.500 g of the dried sample was accurately weighed and charged into a conical flask equipped with a ground-in stopper. On the other hand, 0.100 g of DL-β-aminoisobutyric acid was accurately weighed and dissolved by adding a phosphate buffer (pH 7.4) to prepare a stock solution having an accurate volume of 1000 mL. The stock solution in an accurate amount of 50 mL was charged to the conical flask equipped with a ground-in stopper. The flask was shaken at 37±1° C. for 3 hours. The product in the flask was filtered with suction through a 0.65 μm membrane filter. A first filtrate (about 20 mL) was discarded, and a subsequent filtrate (about 10 mL) was taken as a sample solution.

Then, 0.1 mL of the sample solution was accurately weighed and charged in a test tube. A phosphate buffer (pH 8.0) was added in an accurate amount of 5 mL thereto, and the whole was mixed. Thereafter, a solution prepared by dissolving 0.100 g of fluorescamine in 100 mL of acetone (for a non-aqueous titration) was added in an accurate amount of 1 mL, and the whole was mixed and allowed to stand for 15 minutes. The resulting solution was analyzed by fluorometry, and the fluorescence was measured at an exciting wavelength of 390 nm and a fluorescent wavelength of 475 nm.

A standard curve was prepared by producing 100 mL of a mixture of 0 mL, 15 mL, 50 mL, 75 mL, and 100 mL of the DL-β-aminoisobutyric acid stock solution and the balance of a phosphate buffer (pH 7.4), stirring and filtering the mixture, charging the resulting filtrate in an accurate amount of 0.1 mL to a test tube, adding a phosphate buffer (pH 8.0) in an accurate amount of 5 mL, mixing the whole, adding a solution (an accurate amount: 1 mL) prepared by dissolving 0.100 g of fluorescamine in 100 mL of acetone (for a non-aqueous titration), mixing the whole, allowing to stand for 15 minutes, analyzing the resulting solution by fluorometry, and measuring the fluorescence at an exciting wavelength of 390 nm and a fluorescent wavelength of 475 nm. Finally, an amount (mg/dL) of remaining DL-β-aminoisobutyric acid in the solution was calculated, using the standard curve.

To measure a dependence on an amount of the porous spherical carbonaceous substance sample, the same procedures were repeated except that an amount of the porous spherical carbonaceous substance sample used was 0.500 g, and the test fluorescence was measured and the amount of remaining DL-β-aminoisobutyric acid in the solution was calculated as above.

(3) The Selective Adsorption Rate

The selective adsorption rate was calculated from an amount of remaining α-amylase in the solution in the adsorption test of α-amylase wherein an amount of the carbonaceous adsorbent used was 0.500 g, and an amount of remaining DL-β-aminoisobutyric acid in the solution in the adsorption test of DL-β-aminoisobutyric acid, wherein an amount of the carbonaceous adsorbent used was 0.500 g, using an equation:

$$A=(10-Tr)/(10-Ur)$$

wherein A denotes the selective adsorption rate, and Tr denotes an amount of remaining DL-β-aminoisobutyric acid in the solution, and Ur denotes an amount of remaining α-amylase in the solution.

Example 1

Petroleum pitch (68 kg) (softening point=210° C.; quinoline insoluble contents=not more than 1% by weight; ratio of hydrogen atoms/carbon atoms=0.63) and naphthalene (32 kg) were charged into an autoclave (internal volume=300 L) equipped with stirring fans, melted at 180° C., and mixed. The mixture was extruded at 80 to 90° C. to form string-like shaped products. Then, the string-like shaped products were broken so that a ratio of a diameter to a length became about 1 to 2.

The resulting broken products were added to an aqueous solution containing 0.23% by weight of polyvinyl alcohol (saponification value=88%) and heated to 93° C., and dispersed with stirring to be spheroidized. Then, the whole was cooled by replacing the polyvinyl alcohol aqueous solution with water, at 20° C. for 3 hours, whereby the pitch was solidified and naphthalene crystals were precipitated, and a slurry of spherical shaped products of pitch was obtained.

After most of the water was removed by filtration, naphthalene in pitch was extracted and removed with n-hexane at an amount about 6 times that of the spherical shaped products of pitch. The resulting porous spherical pitch was heated to 235° C. by passing a heated air in a fluidized bed, and allowed to stand at 235° C. for 1 hour to thereby be oxidized, and a porous spherical oxidized pitch was obtained, which is non-fusible to heat.

Thereafter, the resulting porous spherical oxidized pitch was activated in a fluidized bed at 900° C. for 170 minutes by a nitrogen gas atmosphere containing 50% by volume of steam to obtain a spherical activated carbon. Further, the resulting spherical activated carbon was oxidized in a fluidized bed at 470° C. for 195 minutes by a nitrogen-oxygen atmosphere containing 18.5% by volume of oxygen, and reduced in a fluidized bed at 900° C. for 17 minutes by a nitrogen gas atmosphere, to obtain a porous spherical carbonaceous substance.

The properties of the resulting carbonaceous substance are listed in Tables 1 and 2.

Example 2

The procedure described in Example 1 was repeated, except that the activating time of the porous spherical oxidized pitch was 80 minutes, to obtain the porous spherical carbonaceous substance. The properties of the resulting carbonaceous substance are listed in Tables 1 and 2.

Example 3

The procedure described in Example 1 was repeated, except that the activating time of the porous spherical oxidized pitch was 120 minutes, to obtain the porous spherical carbonaceous substance. The properties of the resulting carbonaceous substance are listed in Tables 1 and 2.

Example 4

The procedure described in Example 1 was repeated, except that the activating time of the porous spherical oxidized pitch was 240 minutes, to obtain the porous spherical carbonaceous substance. The properties of the resulting carbonaceous substance are listed in Tables 1 and 2.

Example 5

The procedure described in Example 1 was repeated, except that the temperature of the cooling water for precipitating the pitch and naphthalene crystals was 25° C., to obtain the porous spherical carbonaceous substance. The properties of the resulting carbonaceous substance are listed in Tables 1 and 2.

Comparative Example 1

The procedure described in Example 1 was repeated, except that, instead of activating the porous spherical oxidized pitch, a temperature of the porous spherical oxidized pitch was raised to 900° C. over 90 minutes in a fluidized bed by a nitrogen stream, and after the temperature reached 900° C., the pitch was allowed to stand to cool, to obtain the porous spherical carbonaceous substance. The properties of the resulting carbonaceous substance are listed in Tables 1 and 2.

Comparative Example 2

The procedure described in Example 1 was repeated, except that the temperature of the cooling water for precipitating the pitch and naphthalene crystals was 30° C., and the temperature for oxidizing the porous spherical pitch to the porous spherical oxidized pitch was 260° C., to obtain the porous spherical carbonaceous substance. The properties of the resulting carbonaceous substance are listed in Tables 1 and 2.

Comparative Example 3

The porous spherical carbonaceous substance obtained in Example 1 was ground by a grinder to a powder material having an average particle size of 20 µm to obtain a powdery porous carbonaceous substance. The properties of the resulting carbonaceous substance are listed in Tables 1 and 2.

Comparative Example 4

The procedure described in Example 1 was repeated, except that the reduction treatment of the spherical activated carbon was not carried out, to obtain the porous spherical carbonaceous substance. The properties of the resulting carbonaceous substance are listed in Tables 1 and 2.

Comparative Example 5

The procedure described in Example 1 was repeated, except that the oxidization treatment and the reduction treatment of the spherical activated carbon were not carried out, to obtain the porous spherical carbonaceous substance. The properties of the resulting carbonaceous substance are listed in Tables 1 and 2.

Comparative Example 6

For comparison, a medical activated carbon listed in the Japanese Pharmacopoeia was evaluated in the same manner. The medical activated carbon is a powdery carbon. The results are listed in Tables 1 and 2.

TABLE 1

| | Raw Material | Activation Time min | SSA $m^2/g$ | Pore volume mL/g | Average particle diameter µm |
|---|---|---|---|---|---|
| Example 1 | pitch | 170 | 1300 | 0.08 | 350 |
| Example 2 | pitch | 80 | 800 | 0.06 | 350 |
| Example 3 | pitch | 120 | 1100 | 0.07 | 350 |
| Example 4 | pitch | 240 | 1800 | 0.09 | 350 |
| Example 5 | pitch | 170 | 1320 | 0.09 | 350 |
| Comparative Example 1 | pitch | 0 | 540 | 0.03 | 350 |
| Comparative Example 2 | pitch | 170 | 1350 | 0.12 | 350 |
| Comparative Example 3 | pitch | 170 | 1350 | — | 20 |
| Comparative Example 4 | pitch | 170 | 1300 | 0.15 | 350 |
| Comparative Example 5 | pitch | 170 | 1300 | 0.09 | 350 |
| Comparative Example 6 | Medical activated carbon | — | 900 | 0.42 | 40 |

The pore volume in Table 1 was determined by a mercury injection method and corresponds to a volume of pores having a diameter of 20 to 15000 nm.

TABLE 2

| | Total amount of acidic groups meq/g | Total amount of basic groups meq/g | Amount of remaining α-amylase in solutions (mg/dL) 0.125 g | Amount of remaining α-amylase in solutions (mg/dL) 0.50 g | Amount of remaining DL-β-aminoisobutyric acid in solutions (mg/dL) 0.50 g | Amount of remaining DL-β-aminoisobutyric acid in solutions (mg/dL) 2.50 g | Selective adsorption rate |
|---|---|---|---|---|---|---|---|
| Example 1 | 0.67 | 0.54 | 8.47 | 7.19 | 5.24 | 0.14 | 1.69 |
| Example 2 | 0.62 | 0.47 | 8.77 | 7.83 | 6.19 | 0.65 | 1.76 |
| Example 3 | 0.65 | 0.50 | 8.61 | 7.55 | 5.72 | 0.32 | 1.75 |
| Example 4 | 0.68 | 0.57 | 8.63 | 7.02 | 5.17 | 0.15 | 1.62 |
| Example 5 | 0.67 | 0.54 | 8.38 | 7.15 | 5.23 | 0.14 | 1.67 |
| Comparative Example 1 | 0.52 | 0.36 | 9.06 | 8.59 | 8.59 | 5.42 | 1.00 |
| Comparative Example 2 | 0.67 | 0.54 | 7.85 | 5.56 | 5.25 | 0.14 | 1.07 |
| Comparative Example 3 | 0.68 | 0.55 | 7.78 | 5.10 | 5.21 | 0.13 | 0.98 |
| Comparative Example 4 | 2.48 | 0.06 | 6.33 | 2.56 | 7.70 | 4.67 | 0.31 |
| Comparative Example 5 | 0.18 | 0.58 | 8.63 | 7.68 | 8.46 | 4.30 | 0.66 |
| Comparative Example 6 | 0.65 | 0.44 | 0.04 | 0.00 | 8.99 | 5.70 | 0.10 |

FIG. 1 shows a relationship between the selective adsorption rate and the pore volume of the carbonaceous adsorbent, for seven (7) carbonaceous adsorbents prepared in Examples 1 to 5 and Comparative Examples 1 to 2. The seven adsorbents have similar properties other than the pore volume, and were prepared by similar methods. As apparent from FIG. 1, the carbonaceous adsorbents having the pore volume of 0.04 to 0.10 mL/g exhibit an excellent selective adsorption rate. Further, it is manifest from Table 2 and FIG. 1 that the porous spherical carbonaceous adsorbent of the present invention has an excellent and selective adsorption rate.

Examples to Confirm Safety (1) Confirmation of Safety in Single Dose

The adsorbent prepared in Example 1 according to the present invention was used as a sample. The sample was forcefully orally administered to five male SD rats (6 weeks old) at a dosage of 5 g/kg/day by a flexible disposable catheter for a rat. On the eighth day after the administration day, the survival, behavior, aspect, and change of weight were observed. On the ninth day after the administration day, an autopsy was carried out. A liver, kidneys and gastrointestinal tracts were visually observed, and a weight of each of the liver and kidneys was measured.

No general abnormality was observed in each rat, shortly after the administration and during the observation period. No suppression of body weight increase, and no change in organ weight was observed. Further, in an autopsy, no change was visually observed in each rat. No abnormality was visually observed in the gastrointestinal tracts of each rat. As above, no toxicological change was observed in a test of single dose of the adsorbent according to the present invention.

(2) Confirmation of Safety in Repeated Doses

The adsorbent prepared in Example 1 according to the present invention was used as a sample. A mixed feed was prepared so that a dose became 5 g/kg/day. For 28 days, five male SD rats (6 weeks old) were allowed to freely take the feed for 24 hours. While the administration was carried out, the survival, behavior, aspect, and change of weight were observed. On 29th day after the administration started, a blood sample was taken and an autopsy was carried out. The liver, kidneys and gastrointestinal tracts were visually observed, and a weight of each of the liver and kidneys was measured. Protein fractions in serum, total cholesterol, and inorganic phosphorus were measured by a hemochemical analysis.

No change in general conditions was observed in each rat during the testing period. A body weight of each rat and an amount of feed taken were satisfactorily increased. An average dosage was calculated from the amount of feed taken to about 5 g/kg/day. No particular change was observed in organ weights or hemochemical analysis. Further, in an autopsy, no change that appeared to have been caused by administering the adsorbent of the present invention was visually observed in each rat. No abnormality was visually observed in the gastrointestinal tracts of each rat. As above, no toxicological change was observed for 28 days in a test of a repeated dose of the adsorbent according to the present invention.

Pharmacological Example (1) Ameliorating Function of a Renal Disease

The adsorbent prepared in Example 1 according to the present invention was used as a sample. Eighteen rats with a renal disorder caused by subtotal nephrectomy were divided into two groups, a control group (9 rats) and a present-adsorbent-administering group (9 rats), so that there was no major imbalance therebetween. For 19 weeks, a normal feed was administered to the rats in the control group, whereas the normal feed and the adsorbent of the present invention (in an amount of 0.4 g/day per 100 g of a body weight) were orally administered to the rats in the administering group. After the administration, renal functions, i.e., a creatinine clearance, and a serum creatinine value were evaluated, and an amount of proteins in urine after urine collection for 24 hours was analyzed. Further, a lesion in a kidney was examined by a PAS-stained specimen. For a statistical test between the groups, a t-test was used.

In the control group, the creatinine clearance was 0.168±0.031 (average±SD) mL/min/100 g weight, the serum creatinine value was 1.5±0.2 mg/dL, and the amount of urinary proteins excreted was 118±43 mg/day. Whereas, in the administering group, the creatinine clearance was 0.217±0.042 (average±SD) mL/min/100 g weight, the serum creatinine value was 1.2±0.1 mg/dL, and the amount of urinary proteins excreted was 64±37 mg/day. The improvement was statistically significant ($p<0.05$).

A pathologic-histological examination of the kidney revealed that lesions in a glomerulus and a stroma were clearly inhibited in the administering group, in comparison with the control group.

Therefore, conditions of the renal disease were definitely ameliorated in the present-adsorbent-administering group in comparison with the control group.

(2) Ameliorating Function of a Liver Disease

The adsorbent prepared in Example 1 according to the present invention was used as a sample. Fourteen rats with hepatitis induced by carbon tetrachloride were divided into two groups, a control group (7 rats) and a present-adsorbent-administering group (7 rats), so that there was no major imbalance therebetween. For 10 weeks, a normal feed was administered to the rats in the control group, whereas a mixed feed containing 5% adsorbent of the present invention were administered to the rats in the administering group. A prolylhydroxylase (PH) in serum was measured as an index of liver fibrosis, and ICG (indocyanine green) tolerance test was carried out to examine a liver function, 0 week, 9 weeks, and 10 weeks after the administration started. For a statistical test between the groups, a t-test was used.

In the control group, the prolylhydroxylase (PH) in serum was 832.3±517.5 (average±SD) ng/mL after 9 weeks, and 854.6±575.6 ng/mL after 10 weeks: whereas, in the present-adsorbent-administering group, the prolylhydroxylase (PH) in serum was 435.0±138.0 (average±SD) ng/mL after 9 weeks, and 417.2±255.6 ng/mL after 10 weeks. Although a statistical significance was not found, there was a tendency that lower values were observed in the administering group in comparison with the control group.

In the control group, ICG tolerance test was 1.02±0.16 (average±SD) mg/dL after 9 weeks, and 0.78±0.14 mg/dL after 10 weeks, whereas, in the present-adsorbent-administering group, ICG tolerance test was 0.49±0.02 (average±SD) mg/dL after 9 weeks, and 0.44±0.06 mg/dL after 10 weeks. In the control group, a remaining of added ICG in blood was observed, whereas, in the adsorbent-administering group, the such a remaining was significantly inhibited.

As above, it is strongly suggested that the adsorbent of the present invention may improve a liver dysfunction accompanied with fibrosis, and inhibit any progress from hepatitis to liver cirrhosis.

Application Example to Liver Dysfunction (1) A male patient (79 years old) suffering from a liver dysfunction showed 47 units of GOT (glutamic-oxaloacetic transaminase) and 66 units of GPT (glutamic-pyruvic transaminase). An oral administration of the adsorbent of the present invention was started and continued to the patient at 3 g/day. Four months later, a GOT was lowered to 21 units, and a GPT was lowered to 24 units. The administration was continued, and 7 months after the beginning of the administration, the GOT was lowered to 18 units, and the GPT was lowered to 21 units. As above, an improvement of the liver function was observed.

(2) A male patient (46 years old) suffering from chronic hepatitis showed 169 units of GOT and 353 units of GPT. An oral administration of the adsorbent of the present invention was started and continued to the patient at 6 g/day. One month later, the GOT was lowered to 15 units, and the GPT was lowered to 15 units, and six months later, the GOT was lowered to 14 to 22 units, and the GPT was lowered to 14 to 21 units. As above, a stable condition was observed and an improvement of the liver function was observed.

Application Example to Renal Dysfunction (1) A male patient (73 years old) suffering from a chronic renal failure showed 3.1 mg/dL of S-Cr, and 64.8 mg/dL of BUN. An oral administration of the adsorbent of the present invention was started and continued to the patient at 6 g/day. One month later, the S-Cr was lowered to 1.5 mg/dL, and the BUN was lowered to 17.2 mg/dL. The administration was continued, and 6 months after the beginning of the administration, the S-Cr was lowered to 1.5 to 2.2 mg/dL, and the BUN was lowered to 17.0 to 29.1 mg/dL. As above, a stable condition was observed and an improvement of the renal function was observed.

(2) A male patient (42 years old) suffering from a chronic renal failure caused by glomerular nephritis showed 2.9 mg/dL of S-Cr, and 55 mg/dL of BUN. An oral administration of the adsorbent of the present invention was started and continued to the patient at 6 g/day. Two months later, the S-Cr was lowered to 2.2 mg/dL, and the BUN was lowered to 52 mg/dL. The administration was continued, and 6 months after the beginning of the administration, the S-Cr was lowered to 1.8 mg/dL, and the BUN was lowered to 42 mg/dL. As above, an improvement of the renal function was observed.

Effects on Diabetic Nephropathy (1) Procedure for Test

Streptozotocin (Sigma Chemical) at a dosage of 40 mg/kg was intravenouly administered into each 6-week-old male Jcl-Sprague-Dawley rat having a body weight of 300 g (CLEA Japan, Inc.) to develop diabetes. After two weeks from the administration of streptozotocin, a right kidney was removed from each rat in which the blood sugar level was 250 mg/dL or more. For 13 weeks after two weeks had passed from the surgical removal of the right kidney, a high-fat diet was administered to obtain 26 diabetic rats having a blood sugar level of 268 to 746 mg/dL. As a non-diabetic rat for a control, 7 normal rats, and 7 rats in which the right kidney [Kidney(r)-removed control rats] was removed were used.

After 13 weeks had passed from the point two weeks after the surgical removal of the right kidney, a mixture of the adsorbent of the present invention obtained in Example 1 at a dosage of 4 g/kg/day with a powdery high-fat diet (Labo MR-DBT; Nosan Corporation) was orally administered to 13 diabetic rats for 10 weeks. The remaining 13 diabetic rats were used as a control, and allowed to take only the powdery high-fat diet.

From the beginning of administration of the adsorbent of the present invention, a feed intake and weight were measured once per two days and once per a week, respectively, and a blood pressure, a biochemical analysis of serum, and a kidney function test were carried out after 13, 18, and 23 weeks.

The blood pressure was measured by an automated sphygmomanometer (BP-98A; Softron Co. Ltd.). The blood sugar value was measured with Synchron CX3delta (Beckman Instruments, Inc.). $HbA_{1c}$ was measured with DCA2000HbA$_{1c}$ Analyzer (Bayer-Sankyo). An amount of proteins in urine was measured by a pyrogallol red method (Micro TP-test; Wako Pure Chemical Industries) and calculated by a conventional method. A creatinine clearance value was calculated by a conventional method from a concentration of creatinine measured with Synchron CX3delta (Beckman Instruments, Inc.).

(2) Results of Test

Administration of the adsorbent of the present invention did not affect the weight, feed intake, blood sugar level by diabetes, and $HbA_{1c}$.

Administration of the adsorbent of the present invention significantly repressed an elevated blood pressure in diabetic rats after 23 weeks. The blood pressure (average±standard error) is shown in Table 3.

TABLE 3

| Administering group | No. of samples | Blood pressure (mmHg) | | |
|---|---|---|---|---|
| | | 13 weeks | 18 weeks | 23 weeks |
| Normal rats | 7 | 139 ± 9 | 134 ± 9 | 129 ± 18 |
| Kidney(r)-removed control rats | 7 | 134 ± 8 | 137 ± 6 | 138 ± 9 |
| Diabetic rats | 13 | 145 ± 11 | 147 ± 14 | 152 ± 9 |
| Diabetic + adsorbent-administering rats | 13 | 146 ± 10 | 140 ± 6 | 143 ± 11* |

A statistical significance with respect to the blood pressure of the diabetic rats (Student's t-test)
*p < 0.05 (Significance with respect to the diabetic rat)

Administration of the adsorbent of the present invention tended to repress an elevated creatinine clearance value in diabetic rats. The creatinine clearance value (average±standard error) in each group is shown in Table 4.

TABLE 4

| Administering group | No. of samples | Creatinine clearance value (mL/min/100 g weight) | | |
|---|---|---|---|---|
| | | 13 weeks | 18 weeks | 23 weeks |
| Normal rats | 7 | 0.48 ± 0.120 | 0.53 ± 0.159 | 0.45 ± 0.063 |
| Kidney(r)-removed control rats | 7 | 0.41 ± 0.097 | 0.41 ± 0.057 | 0.342 ± 0.02 |
| Diabetic rats | 13 | 0.45 ± 0.011 | 0.59 ± 0.411 | 0.46 ± 0.061 |
| Diabetic + adsorbent-administering rats | 13 | 0.42 ± 0.092 | 0.46 ± 0.095 | 0.42 ± 0.060 |

Administration of the adsorbent of the present invention significantly decreased an elevated amount of proteins in urine in diabetic rats after 18 weeks. The amount of proteins in urine (average±standard error) in each group is shown in Table 5.

TABLE 5

| Administering group | No. of samples | Amount of proteins in urine (mg/day) | | |
|---|---|---|---|---|
| | | 13 weeks | 18 weeks | 23 weeks |
| Normal rats | 7 | 10.6 ± 3.58 | 10.4 ± 4.18 | 9.7 ± 3.14 |
| Kidney(r)-removed control rats | 7 | 12.4 ± 3.12 | 12.2 ± 4.88 | 12.7 ± 9.52 |
| Diabetic rats | 13 | 8.9 ± 4.04 | 15.2 ± 8.38 | 22.3 ± 19.4 |
| Diabetic + adsorbent-administering rats | 13 | 9.3 ± 4.61 | 8.2 ± 4.49** | 8.08 ± 2.93* |

A statistical significance with respect to the amount of proteins in urine of the diabetic rats (Student's t-test)
*p < 0.05 (Significance with respect to the diabetic rat)
**p < 0.02 (Significance with respect to the diabetic rat)

Effects on Liver Fibrosis (1) Procedure for Test

A choline-free powdery diet containing amino acids (Dyets; USA) was administered to 10 male Wistar rats (6-week-old) having body weights of 130 to 150 g (SLC) for two weeks. Eight rats in which liver fibrosis was developed were selected by measuring GOT and GPT after two weeks, and divided into a control group (4 rats) and a presentadsorbent-administering group (4 rats), so that there was no major imbalance therebetween.

The choline-free powdery diet containing amino acids was administered to rats in the control group. A feed obtained by mixing 4% (weight/weight %) of the adsorbent of the present invention obtained in Example 1 with the choline-free powdery diet containing amino acids was administered to the present-adsorbent-administering group. Observation of both groups was carried out for 16 weeks.

A feed intake, weight, and GOT and GPT were measured three times per a week, once per a week, and once per two weeks, respectively. Further, an ICG (indocyanine green) test was carried out after 11 weeks (from the administration of the adsorbent of the present invention), and a rate of liver fibrosis was measured after 16 weeks (from the administration of the adsorbent of the present invention).

GOT and GPT were measured with Automatic super dry system spotchem SP-4410. The ICG test was carried out by administering indocyanine green (Diagnogreen Inj.; Daiichi Pharmaceutical) at a dose of 5 mg/kg weight, taking a blood sample after 15 minutes, and calculating the difference between absorbances before and after the administration of indocyanine green. The rate of liver fibrosis was measured by distinguishing a pathologic tissue stained by Azan using an automatic image analyzer under the light microscope (Image Analyzer V10; Toyobo).

(2) Results of Test

Administration of the adsorbent of the present invention did not affect the weight, feed intake, GOT, and GPT.

The present-adsorbent-administering group exhibited a statistically significant lower value in the ICG test after 11 weeks, in comparison with the control group. The ICG value (average±standard error) in each group is shown in Table 6.

TABLE 6

|  | No. of samples | ICG value (mg/dL) 11 weeks |
| --- | --- | --- |
| Control rats | 4 | 3.544 ± 0.981 |
| Adsorbent-administering rats | 4 | 1.636 ± 0.300* |

A statistical significance with respect to the ICG value in the control rats (Student's t-test)
*p < 0.01 (Significance with respect to the control rats)

The present-adsorbent-administering group exhibited a statistically significant lower value in the rate of liver fibrosis after 16 weeks, in comparison with the control group, and repressed liver fibrosis. The rate of liver fibrosis (average±standard error) in each group is shown in Table 7.

TABLE 7

|  | No. of samples | Rate of liver fibrosis (%) 16 weeks |
| --- | --- | --- |
| Control rats | 4 | 5.511 ± 0.695 |
| Adsorbent-administering rats | 4 | 2.457 ± 0.974* |

A statistical significance with respect to the rate of liver fibrosis in the control rats (Student's t-test)
*p < 0.002 (Significance with respect to the control rats)

As above, in comparison with the oral adsorbent disclosed in Japanese Examined Patent Publication (Kokoku) No. 62-11611, the oral adsorbent comprising the porous spherical carbonaceous substance according to the present invention can maintain an excellent adsorbability of β-aminoisobutyric acid, which is a toxic substance in a renal disease, while lowering the adsorbability of useful substances, for example, digestive enzymes. Further, the oral adsorbent of the present invention has few side effects such as constipation, and exhibits an excellent function as an oral medicament for treating a liver or renal disease, as the oral adsorbent disclosed in Japanese Examined Patent Publication (Kokoku) No. 62-11611.

As above, the present invention was explained with reference to particular embodiments, but modifications and improvements obvious to those skilled in the art are included in the scope of the present invention.

What is claimed is:

1. An adsorbent for an oral administration, comprising a porous spherical carbonaceous substance wherein a diameter is 0.01 to 1 mm, a specific surface area determined by a BET method is 700 $m^2/g$ or more, a volume of pores having a pore diameter of 20 to 15000 nm is from not less than 0.04 mL/g to less than 0.10 mL/g, a total amount of acidic groups is 0.30 to 1.20 meq/g, and a total amount of basic groups is 0.20 to 1.00 meq/g.

2. The adsorbent according to claim 1, wherein the diameter is 0.02 to 0.8 mm.

3. The adsorbent according to claim 1, wherein the specific surface area determined by a BET method is 700 to 2500 $m^2/g$.

4. A pharmaceutical composition comprising a porous spherical carbonaceous substance wherein a diameter is 0.01 to 1 mm, a specific surface area determined by a BET method is 700 $m^2/g$ or more, a volume of pores having a pore diameter of 20 to 15000 nm is from not less than 0.04 m/g to less than 0.10 mL/g, a total amount of acidic groups is 0.30 to 1.20 meq/g, and a total amount of basic groups is 0.20 to 1.00 meq/g, and a pharmaceutically acceptable carrier or diluent.

5. A method for treating a renal disease, comprising administering to a subject in need thereof, a porous spherical carbonaceous substance wherein a diameter is 0.01 to 1 mm, a specific surface area determined by a BET method is 700 $m^2/g$ or more, a volume of pores having a pore diameter of 20 to 15000 nm is from not less than 0.04 mL/g to less than 0.10 mL/g, a total amount of acidic groups is 0.30 to 1.20 meq/g, and a total amount of basic groups is 0.20 to 1.00 meq/g, in an amount effective thereof.

6. The method according to claim 5, wherein the renal disease is a disease selected from the group consisting of chronic renal failure, acute renal failure, chronic pyelonephritis, acute pyelonephritis, chronic nephritis, acute nephritic syndrome, acute progressive nephritic syndrome, chronic nephritic syndrome, nephrotic syndrome, nephrosclerosis, interstitial nephritis, tubulopathy, lipoid nephrosis, diabetic nephropathy, renovascular hypertension, and hypertension syndrome, and secondary renal diseases caused by these primary diseases.

7. The method according to claim 5, wherein the renal disease is a light renal failure before a dialysis therapy.

8. A method for treating a liver disease, comprising administering to a subject in need thereof, a porous spherical carbonaceous substance wherein a diameter is 0.01 to 1 mm, a specific surface area determined by a BET method is 700 $m^2/g$ or more, a volume of pores having a pore diameter of 20 to 15000 nm is from not less than 0.04 mL/g to less than 0.10 mL/g, a total amount of acidic groups is 0.30 to 1.20 meq/g, and a total amount of basic groups is 0.20 to 1.00 meq/g, in an amount effective thereof.

9. The method according to claim 8, wherein the liver disease is a disease selected from the group consisting of fulminant hepatitis, chronic hepatitis, viral hepatitis, alcoholic hepatitis, hepatic fibrosis, liver cirrhosis, hepatic cancer, autoimmune hepatitis, drug allergic hepatopathy, and primary biliary cirrhosis.

10. The method according to claim 8, wherein the liver disease is a disease selected from the group consisting of tremor, encephalopathia, dysbolism, and dysfunction.

11. A process for manufacturing an adsorbent for oral administration, comprising the steps of:

oxidizing a spherical activated carbon wherein a diameter is 0.01 to 1 mm, a specific surface area determined by a BET method is 700 m$^2$/g or more, and a volume of pores having a pore diameter of 20 to 15000 nm is from not less than 0.04 mL/g to less than 0.10 mL/g, in a temperature range of 300 to 800° C. in an atmosphere containing 0.1 to 50% by volume of oxygen, and reducing an oxidized spherical activated carbon in a temperature range of 800 to 1200° C. in an atmosphere of a non-oxidizable gas.

* * * * *

UNITED STATES PATENT AND TRADEMARK OFFICE
CERTIFICATE OF CORRECTION

PATENT NO. : 6,830,753 B2
DATED : December 14, 2004
INVENTOR(S) : Naohiro Sonobe, Michihito Ise and Susumu Morimoto It is certified that error appears in the above-identified patent and that said Letters Patent is hereby corrected as shown below:

<u>Column 18,</u>
Line 23, claim 4 should read as follows:
      4. A pharmaceutical composition comprising a porous spherical carbonaceous substance wherein a diameter is 0.01 to 1 mm, a specific surface area determined by a BET method is 700 $m^2$/g or more, a volume of pores having a pore diameter of 20 to 15000 nm is from not less than 0.04 mL/g to less than 0.10 mL/g, a total amount of acidic groups is 0.30 to 1.20 meq/g, and a total amount of basic groups is 0.20 to 1.00 meq/g, and a pharmaceutically acceptable carrier or diluent.

Signed and Sealed this

Twenty-eighth Day of June, 2005

JON W. DUDAS
*Director of the United States Patent and Trademark Office*